US007687075B2

(12) United States Patent
Skiendzielewski et al.

(10) Patent No.: US 7,687,075 B2
(45) Date of Patent: Mar. 30, 2010

(54) COLONIC PURGATIVE COMPOSITION WITH SOLUBLE BINDING AGENT

(75) Inventors: Stephen Skiendzielewski, Norristown, PA (US); Martin Rose, Bethesda, MD (US); Ngoc Do, Bel Air, MD (US)

(73) Assignee: Salix Pharmaceuticals, Ltd., Morrisville, NC (US)

(*) Notice: Subject to any disclaimer, the term of this patent is extended or adjusted under 35 U.S.C. 154(b) by 1314 days.

(21) Appl. No.: 10/988,693

(22) Filed: Nov. 16, 2004

(65) Prior Publication Data

US 2005/0129781 A1    Jun. 16, 2005

Related U.S. Application Data

(60) Provisional application No. 60/523,142, filed on Nov. 19, 2003.

(51) Int. Cl.
*A61K 33/42* (2006.01)
*A61K 9/20* (2006.01)
*A61K 31/66* (2006.01)

(52) U.S. Cl. .................... 424/606; 424/464; 514/75
(58) Field of Classification Search .......... 424/606, 424/464; 514/75
See application file for complete search history.

(56) References Cited

U.S. PATENT DOCUMENTS

| 3,121,663 A | 2/1964 | Parker |
| 3,202,578 A | 8/1965 | Parker |
| 3,976,773 A | 8/1976 | Curran |
| 4,321,263 A | 3/1982 | Powell et al. |
| 4,812,311 A | 3/1989 | Uchtman |
| 4,828,842 A | 5/1989 | Furst et al. |
| 4,999,200 A | 3/1991 | Casillan |
| 5,077,048 A | 12/1991 | Kimura et al. |
| 5,338,564 A * | 8/1994 | Meyer et al. ............... 426/612 |
| 5,397,573 A * | 3/1995 | Kajs et al. ............... 424/451 |
| 5,516,524 A | 5/1996 | Kais et al. |
| 5,616,346 A | 4/1997 | Aronchick |
| 5,710,183 A | 1/1998 | Halow |
| 5,997,906 A | 12/1999 | Wood et al. |
| 6,048,901 A | 4/2000 | Cleveland et al. |
| 6,162,464 A | 12/2000 | Jacob et al. |

FOREIGN PATENT DOCUMENTS

| WO | WO 87/00754 | 2/1987 |
| WO | WO 02/26222 A2 | 4/2002 |
| WO | WO 03/092589 A2 | 11/2003 |
| WO | WO 2004/006833 A2 | 1/2004 |

OTHER PUBLICATIONS

Gennaro, Remington's Pharmaceutical Sciences, 1990, p. 1393 and 1635-1637.*

(Continued)

*Primary Examiner*—Johann R Richter
*Assistant Examiner*—Abigail Fisher
(74) *Attorney, Agent, or Firm*—Edwards Angell Palmer & Dodge LLP; Peter F. Corless; Jonathan M. Sparks (57) ABSTRACT

This invention relates to novel colonic purgative compositions in a solid dosage form, comprising at least one purgative and at least one soluble, or soluble, nonfermentable binder, such as polyethylene glycol. Further, this invention relates to methods of using the colonic purgative compositions. The present compositions and methods are designed to improve patient tolerance and compliance, while at the same time improving the quality of bowel cleansing. The formulations and methods of this invention are particularly useful to cleanse the bowel prior to diagnostic and surgical procedures and can also be employed in lower dosages as a laxative to promote elimination and/or to relieve constipation.

48 Claims, 2 Drawing Sheets

OTHER PUBLICATIONS

Rubinstein, Pharmaceutics: The Science of Dosage Form Design, Chapter 18, ed. Aulton, 2002, pp. 304-321.*

Olsson et al., Int. J. Pharmaceutics, 1998, 171, 31-44.*

Aronchick, Craig A. et al., A Novel Tableted Purgative for Colonoscopic Preparation: Efficacy and Aafety Comparisons With Colyte and Fleet Phospho-Soda, Gastrointestinal Endoscopy, vol. 52, No. 3, 2000, pp. 346-352.

American Hospitality Formulary Service Drug Information, 1991, pp. 1730-1732.

George, John. After Merger, Drug Firm Gravitates to Area. Philadelphia Business Journal, Nov. 21, 1997.

George, John. No More Yucky Liquid? Philadelphia Business Journal. Jun. 18, 1999.

George, John. An Easier Pill to Swallow. Philadelphia Business Journal. Sep. 29, 2000.

American Hospital Formulary Service Drug Information, 1991. pp. 1730-1732.

Deuxchaisnes et al. The Treatment of Adult Phosphate Diabetes and Fanconi Syndrome with Neutral Sodium Phosphate. American Jounal of Medicine, vol. 43, Oct. 1967. pp. 508-543.

Remington's Pharmaceutical Sciences. 18th Edition. Chapter 39. pp. 786-787, 1304-1308, and 1635-1638.

Brigitte Stoffer-Vogel et al., Oral Availability of Mesna Tablets, Cancer Chemother Pharmacol (1993) 32: pp. 78-81.

L.Lachman et al., The Theory and Practice of Industrial Pharmacy, 1986, p. 321 and 328.

The United States Pharmacopeia, The National Formulary, 1990, pp. 1265-1267.

The British Pharmaceutical Codex, 1911.

Drug Evaluations Annual 1991, pp. 816-817.

Physician's Desk Reference, 45th Edition, 1991, p. 638.

Indian Pharmaceutical Guide, 17th Edition, 1979, p. 1323.

Remington's Practice of Pharmacy, 1956, pp. 460-461.

Martindale, The Extra Pharmacopoeia, 29th Edition, 1989.

George Gilbert Smith, An Outline of Genito-Urinary Surgery, 1919.

Afridi, S.A. et al., "Prospective, Randomized Trial Comparing A New Sodium Phosphate-Bisacodyl Regimen with Conventional PEG-ES Lavage for Outpatient Colonoscopy Preparation," *Gastrointestinal Endoscopy*, 41(5):485-489 (1995).

Andorsky, R. I. et al., "Colonic Lavage Solution (Polyethylene Glycol Electrolyte Lavage Solution) as a Treatment for Chronic Constipation: A Double-Blind, Placebo-Controlled Study," *The American Journal of Gastroenterology*, 85(3):261-265 (1990).

Attar, A. et al., "Comparison of A Low Dose Polyethylene Glycol Electrolyte Solution with Lactulose for Treatment of Chronic Constipation," *Gut*, 44(2):226-230 (1999).

Balaban, D.H. et al., "Low Volume Bowel Preparation for Colonoscopy: Randomized, Endoscopist-Blinded Trial of Liquid Sodium Phosphate *Versus* Tablet Sodium Phosphate," *The American Journal of Gastroenterology*, 98(4):827-832 (2003).

Børkje, R. et al., "Effectiveness and Acceptability of Three Bowel Cleansing Regimens," *Scandinavian Journal of Gastroenterology*, 26(2):162-166 (1991).

Church, J. M., "Effectiveness of Polyethylene Glycol Antegrade Gut Lavage Bowel Preparation for Colonoscopy—Timing is the Key!" *Diseases of the Colon and Rectum*, 41(10):1223-1225 (1998).

Clarkston, W. et al., "Oral Sodium Phosphate Versus Sulfate-Free Polyethylene Glycol Electrolyte Lavage Solution in Outpatient Preparation for Colonoscopy: A Prospective Comparison," *Gastrointestinal Endoscopy*, 43:42-48 (1996).

Cohen, S. et al., "Prospective, Randomized, Endoscopic-Blinded Trial Comparing Precolonoscopy Bowel Cleansing Methods," *Diseases of the Colon and Rectum*, 37:689-696 (1994).

Dakkak, M. et al., "Short Report: Comparison of Two Orally Administered Bowel Preparations for Colonoscopy—Polyethylene Glycol and Sodium Picosulphate," *Aliment. Pharmacol. Ther*. 6:513-519 (1992).

De Wilt, J.H.W. et al., "Gas Explosion During Colonic Surgery," *J.R. Coll. Surg. Edinb*. 41(6):419 (1996).

Dipalma, J. et al., "Comparison of Reduced Volume Versus Four Liters Sulfate-Free Electrolyte Lavage Solutions for Colonoscopy Colon Cleansing," *The American Journal of Gastroenterology*, 98:2187-2191 (2003).

Dueholm, S. et al., "Preparation for Elective Colorectal Surgery: A Randomized, Blinded Comparison Between Oral Colonic Lavage and Whole-Gut Irrigation," *Diseases of the Colon and Rectum*, 30:360-364 (1987).

Fleites, R. et al., "The Efficacy of Polyethylene Glycol—Elecytrolyte Lavage Solution Versus Traditional Mechanical Bowel Preparation for Elective Colonic Surgery: A Randomized, Prospective, Blinded Clinical Trial," *Surgery*, 98:708-717 (1985).

Frommer, D., "Cleansing Ability and Tolerance of Three Bowel Preparations for Colonoscopy," *Diseases of the Colon and Rectum*, 40:100-104 (1997).

Goldberg, P. et al. "A Study of a New Osmotic Purgative for Colonoscopy," *Surgical Endoscopy*, 9:329-331 (1995).

Golub, R. et al., "Colonoscopic Bowel Preparations—Which One?" *Diseases of the Colon and Rectum*, 38:594-599 (1995).

Hamilton, D. et al., "Sodium Picosulphate Compared with Poly-Ethylene Glycol Solution for Large Bowel Lavage: A Prospective Randomised Trial," 50:73-75 (1996).

Harewood, G.C. et al., "A Prospective, Controlled Assessment of Factors Influencing Acceptance of Screening Colonoscopy," *The American Journal of Gastroenterology*, 97(12):3186-3194 (2002).

Kolts, B. et al., "A Comparison of the Effectiveness and Patient Tolerance of Oral Sodium Phosphate, Castor Oil, and Standard Electrolyte Lavage for Colonoscopy or Sigmoidoscopy Preparation," *The American Jounal of Gastroenterology*, 88:1218-1223 (1993).

Makino, M. et al., "Randomized Comparison of Two Preoperative Methods for Preparation of the Colon: Oral Administration of a Solution of Polyethylene Glycol Plus Electrolytes and Total Parenteral Nutrition," *Hepato-Gastroenterology*, 45:90-94 (1998).

Marshall, J. et al., "Prospective, Randomized Trial Comparing Sodium Phosphate Solution with Polyethylene Glycol-Electrolyte Lavage for Colonoscopy Preparation," *Gastrointestinal Endoscopy*, 39:631-634 (1993).

Price, J.C.. "Polyethylene Glycol" In: *Handbook of Pharmaceutical Excipients*, $3^{rd}$ ed. (A.H. Kibbe ed.). American Pharmaceutical Association, Washington, D.C., pp. 392-398 (2000).

Regev, A. et al., "Comparison of Two Bowel Preparations for Colonoscopy: Sodium Picosulphate with Magnesium Citrate Versus Sulphate-Free Polyethylene Glycol Lavage Solution," *The American Journal of Gastroenterology*, 93:1478-1482 (1998).

Rex, D. et al., "Safety and Efficacy of Two Reduced Dosing Regimens of Sodium Phosphate Tablets for Preparation Prior to Colonoscopy," *Alimentary Pharmacology and Therapeutics*, 16:937-944 (2002).

Rex, D. et al., "Impact of Bowel Preparation on Efficiency and Cost of Colonoscopy," *The American Journal of Gastroenterology*, 97:1696-1700 (2002).

Thomson, A. et al., "Bowel Preparation for Colonoscopy: A Randomized Prospective Trial Comparing Sodium Phosphate and Polyethylene Glycol In a Predominantly Elderly Population," *Journal of Gastroenterology and Hepatology*, 11:103-107 (1996).

Vanner, S. et al., A Randomized Prospective Trial Comparing Oral Sodium Phosphate with Standard Polyethylene Glycol-Based Lavage Solution (Golytely) in the Preparation of Patients for Colonoscopy, *The American Journal of Gastroenterology*, 85:422-427 (1990).

Wolters, U. et al., "Prospective Randomized Study of Preoperative Bowel Cleansing for Patients Undergoing Colorectal Surgery," *British Journal of Surgery*, 81:598-600 (1994).

Ziegenhagen, D. et al., "Addition of Senna Improves Colonoscopy Preparation with Lavage: A Prospective Randomized Trial," *Gastrointestinal Endoscopy*, 37:547-549 (1991).

* cited by examiner

COLONIC PURGATIVE COMPOSITION WITH SOLUBLE BINDING AGENT

This application claims the benefit of priority to U.S. Provisional Patent Application No. 60/523,142, filed Nov. 19, 2003, the disclosure of which is hereby incorporated by reference in its entirety.

FIELD OF THE INVENTION

This invention relates to colonic purgative formulations in solid dosage form and their use. In certain embodiments of this invention, the formulation contains at least one purgative and at least one soluble binder, which significantly improves the visualization of the colon and patient tolerance. In other embodiments of the invention, the formulation is free of insoluble binder or only contains levels of insoluble binder that do not impede the visualization of the colon. The binder may be nonfermentable in certain embodiments of the invention.

BACKGROUND OF THE INVENTION

It is desirable to identify compounds that sufficiently cleanse the colon, but do not cause adverse side effects. It is also desirable to identify compounds that are used to treat constipation and promote fecal elimination, for instance, but that do not produce uncomfortable or embarrassing side effects such as gas. Additionally, completely clearing the bowel of fecal debris is a necessary prerequisite before a variety of diagnostic and surgical procedures. Cleansing is important, for instance, in order to sufficiently view the gross or microscopic appearance of the colon during colonoscopy. However, the cleansing procedure must also be tolerable to patients so that they are fully compliant with the cleansing process. Poor bowel preparation, due to lack of patient compliance or insufficient cleansing, impacts the efficiency and cost of these procedures, especially if they must be repeated (Rex et al. (2002) *Am. J. Gastroenterol.* 97:1696-1700). Further, patients may not elect to undergo uncomfortable diagnostic procedures, which would significantly reduce early detection of disorders and increase medical costs. (Harewood et al. (2002) *Am. J. Gastroenterol.* 97:3186-3194).

Colonic cleansing is commonly accomplished using lavage with polyethylene glycol-electrolyte solutions. A major disadvantage of this method is that patients are required to ingest a significant amount of liquid volume within a short period of time for purgation. For instance, patients may have to ingest four liters of solution within a period of two to three hours (Afridi et al. (1995) *Gastrointest. Endosc.* 41:485-489). A large number of patients experience significant volume-related discomfort and adverse side effects such as nausea, cramping, and vomiting (Dipalma et al. (2003) *Am. J. Gastroenterol.* 98:2187-2191). Another drawback of these preparations is their salty taste, which may also lead to patient noncompliance and adverse effects. Attempts have been made to make the taste more palatable, for instance by flavoring or reducing salt content. However, these changes did not make the regimen more acceptable to the patient, nor was there an improvement in the quality of colon cleansing (Church (1998) *Dis. Colon Rectum* 41:1223-1225). Such preparations deter patients from colon cancer screening (Harewood et al. (2002) *Am. J. Gastroenterol.* 97:3186-3194).

In an attempt to avoid the problems associated with the high-volume type preparations, smaller-volume aqueous preparations consisting of phosphate salts have been marketed. The phosphate salt solution produces an osmotic effect, causing large amounts of water to be drawn into the bowel, thereby promoting bowel evacuation. Although the lower volume marginally favors these sodium phosphate preparations, adverse side effects such as nausea, vomiting (principally a result of unpalatable taste), abdominal bloating, pain and dizziness were of similar frequency compared to polyethylene glycol-electrolyte lavage (Kolts et al. (1993) *Am. J. Gastroenterol.* 88:1218-1223).

Figure 1:
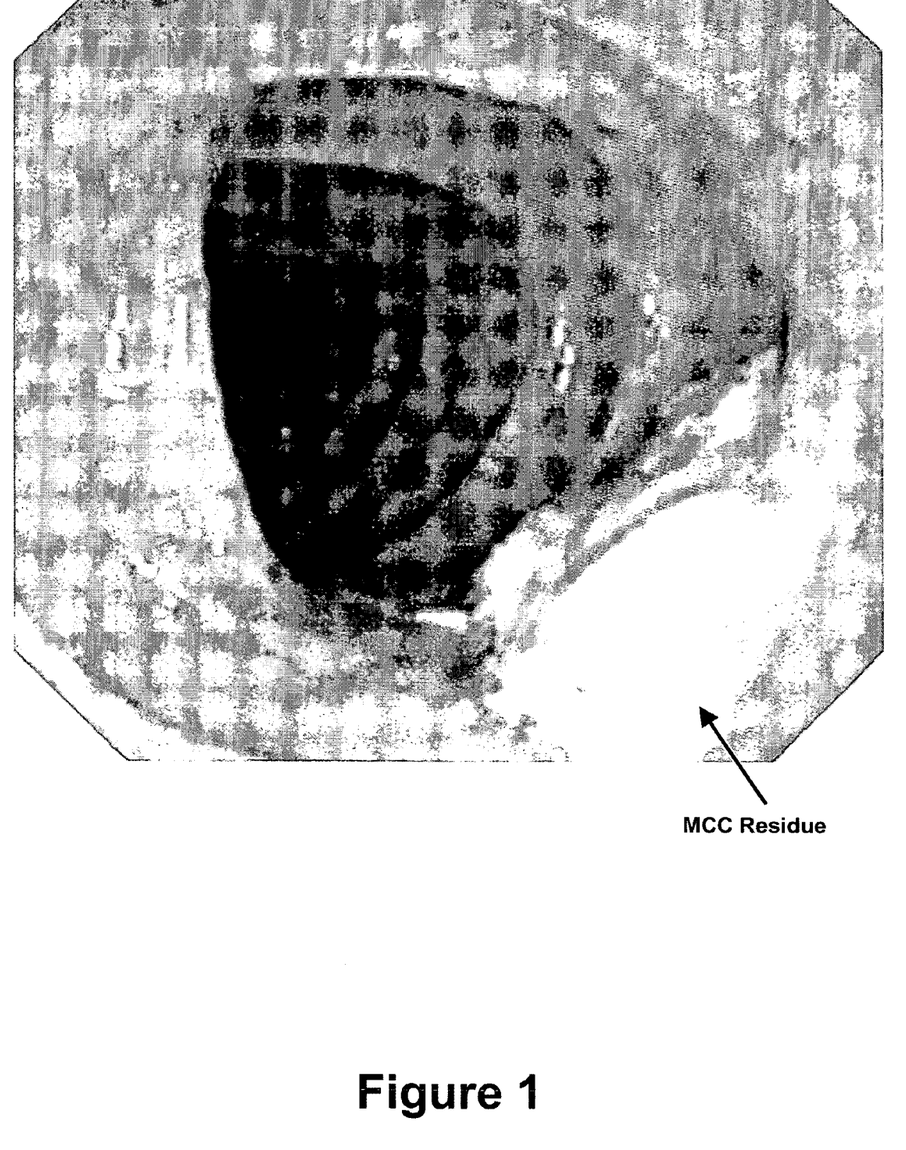
FIG. 1 shows that a prior art composition containing an insoluble binder, microcrystalline cellulose (MCC), leaves a white powdery substance after use for bowel preparation, which significantly impairs visualization of the colon.

Oral tablets containing phosphate salts have been formulated (see U.S. Pat. Nos. 5,616,346 and 6,162,464) to increase preparatory compliance, reduce volume discomfort, and increase patient tolerance. The oral tablet formulation significantly reduced the incidence of gastrointestinal adverse events such as nausea, vomiting, and bloating (Rex et al. (2002) *Aliment Pharmacol. Ther.* 16:937-944). Further, these tablet formulations were significantly better accepted and preferred by patients. Applicants discovered, however, that these formulations were limited in their acceptance by physicians by the presence of visible microcrystalline cellulose (MCC) in the colon, especially in the cecum and ascending colon (FIG. 1). MCC, a purified form of cellulose, is used as a binder in the tablet formulation and is not soluble in the alimentary fluid. Retained MCC can be removed by suctioning or irrigation, so that the colon can be adequately visualized. However, these processes may prolong colonoscopy procedure time (Rex et al. (2002) *Aliment Pharmacol. Ther.* 16:937-944; Balaban et al. (2003) *Am. J. Gastroenterol.* 98:827-832), thereby prolonging the time that the patient is under anesthesia and reducing productivity of physicians (Rex et al. (2002) *Am. J. Gastroenterol.* 97:1696-1700). These tablets, however, were also large and difficult for some to swallow.

Thus, there is need for colonic purgative compositions that can be tolerated by the patient, while also providing quality preparation of the bowel. Further, it is desirable that the composition provides adequate visualization of the colon and structures, without the need for additional removal steps.

It is also desirable to identify a preparation that could be produced easily and used either as a complete purgative or as a laxative for mild catharsis, depending on the dosage administered. Such a dual function composition would be very beneficial.

SUMMARY OF THE INVENTION

The present invention relates to solid dosage form colonic purgative formulations and methods of their use. In one embodiment of the invention, the solid dosage form colonic purgative formulation comprises at least one soluble binder and at least one purgative. In one embodiment of the invention, the binder is nonfermentable. In other embodiments of the invention, the formulation is free of insoluble binder or only contains levels of insoluble binder that do not impede the visualization of the colon.

The at least one purgative may be an osmotic, non-osmotic, or bulk-forming purgative. In one embodiment of the invention, the at least one purgative is an osmotic purgative chosen from sodium phosphate, magnesium phosphate, or a salt thereof. The sodium phosphate salt may be, for example, monobasic sodium phosphate, dibasic sodium phosphate, or tribasic sodium phosphate. In an additional embodiment of the invention, the at least one purgative is a non-osmotic purgative chosen from bisacodyl or picosulfate, for example.

In an additional embodiment of the invention, the colonic purgative formulation comprises at least one non-osmotic purgative and at least one osmotic purgative.

In one embodiment of the invention, the solid dosage form comprises polyethylene glycol as a soluble, nonfermentable binder.

The formulation of the invention may also comprise optional components to improve dosage form characteristics. In one embodiment of the invention, the formulation comprises a lubricant, such as magnesium stearate, to improve the manufacturing process.

The formulation of the invention is a dual function composition. Thus, the present invention encompasses methods of treating gastrointestinal disorders, such as constipation, by providing lower doses of the colonic purgative compositions of the invention as a laxative. The present invention also encompasses methods of complete purgation in order to prepare the colon for a colonoscopy or surgical procedure, by providing higher doses of the compositions of the invention as a complete purgative. Further, the present invention encompasses methods of maintaining the elimination or promoting the elimination of feces from the bowel by providing a colonic purgative composition of the invention.

Additional objects and advantages of the invention will be set forth in part in the description which follows, and in part will be obvious from the description, or may be learned by practice of the invention. The objects and advantages of the invention will be realized and attained by means of the elements and combinations particularly pointed out in the appended claims.

It is to be understood that both the foregoing general description and the following detailed description are exemplary and explanatory only and are not restrictive of the invention, as claimed.

The accompanying drawings, which are incorporated in and constitute part of this specification, together with the description, serve to explain the principles of the invention.

DETAILED DESCRIPTION OF THE INVENTION

A. Definitions

In order that the present invention may be more readily understood, certain terms are first defined. Additional definitions are set forth throughout the detailed description.

The term "purgative" refers to any substance that promotes defecation. Thus, the term purgative encompasses a range of cathartic effects. For instance, the term purgative encompasses mild catharsis, producing Taxation ("partial purgation"), as well as stronger catharsis, providing complete or near-complete emptying of the large bowel ("complete purgation"). In one embodiment of the invention, the term refers to diarrhea. In another embodiment of the invention, the term refers to a softening or loosening of the feces or Taxation. Unless modified by "partial" or "complete," purgative or purgation encompasses the full range of purgative processes, including both complete purgation and laxation ("partial purgation").

The term "osmotic" refers to any substance that promotes the passage of a solvent from a solution of lesser to one of greater solute concentration when the two solutions are separated by a membrane that selectively prevents the passage of solute molecules, but is permeable to the solvent. In the present invention, the term "osmotic" may refer to the ability of a substance to draw water into the intestines.

The term "fermentable" refers to any substance that can be anaerobically catabolized to simpler compounds, usually by bacteria and/or yeast. There are many types of fermentation, differing in the waste products formed and the fermentable substance. Fermentable substances include, but are not limited to, sugars, sugar-alcohols, polysaccharides, lactose, sorbitol, and mannitol. A fermentable substance releases explosive gases upon fermentation. The compound mannitol, for instance, can be fermented by bacteria that are typically resident in the colon of most humans and other mammals, during which hydrogen gas is released. The term "nonfermentable" refers to a substance that is not fermentable.

The term "soluble" or "water soluble" refers to an aqueous solubility that is higher than 1/10,000 (mg/ml). The solubility of a substance, or solute, is the maximum mass of that substance that can be dissolved completely in a specified mass of the solvent, such as water. "Practically insoluble" or "insoluble," on the other hand, refers to an aqueous solubility that is 1/10,000 (mg/ml) or less. Water soluble or soluble substances include, for example, polyethylene glycol.

The term "binder" refers to any substance that exerts a physicochemical attractive force between molecules, and hence may be used in formulation of a dosage form. In one embodiment of the invention, the binder may be mixed with other components of the composition, so that it is distributed uniformly throughout the dosage form. The binder may also provide a matrix upon which any additional components can associate. In one embodiment of the invention, the binder is soluble and nonfermentable. Soluble and nonfermentable binders suitable for use in the invention include, but are not limited to, polyethylene glycol (PEG).

As used herein, the term "salt" or "pharmaceutically acceptable salt" refers to acidic salts formed with inorganic and/or organic acids, as well as basic salts formed with inorganic and/or organic bases. Examples of these acids and bases are well known to those of ordinary skill in the art. Salts according to the present invention may be used in a variety of forms, for example anhydrous or a hydrated crystalline form. The salts may also be those that are physiologically tolerated by a patient.

B. Description of the Invention

Many binders used in solid dosage formulations are insoluble. Applicants discovered that insoluble binders, such as microcrystalline cellulose (MCC), are retained in the colon, hamper visualization of the colon, and prolong colonoscopy procedure time (FIG. 1). Commonly used soluble binders, however, including sugars, sugar-alcohols, and polysaccharides, can be fermented by the intestinal flora. The formation of explosive gases during the fermentation process is an undesirable property during certain surgical and diagnostic procedures involving the colon, such as during a colonoscopy using equipment that may produce a spark. In some documented cases, the presence of these gases during colon electrosurgery has led to explosion (DeWilt et al. (1996) *J. R. Coll. Surg. Edinb.* 41:419). Gases produced during the use of a laxative can also be unpleasant and embarrassing. In one embodiment of the invention, such as to prepare the colon for a colonoscopy, the solid dosage form colonic purgative formulation comprises at least one soluble, nonfermentable binder and at least one purgative. In another embodiment, such as to prepare the colon for a diagnostic procedure that cannot produce a spark in the colon, such as x-ray imaging, virtual colonoscopy (helical CT), and capsule endoscopy, any soluble binder may be used in the composition. In these instances, it is not necessary that the binder or other ingredients be nonfermentable. Soluble, nonfermentable binders may, however, be used in compositions to prepare the colon for procedures that cannot produce a spark.

1. Binders and Purgatives

Figure 2:
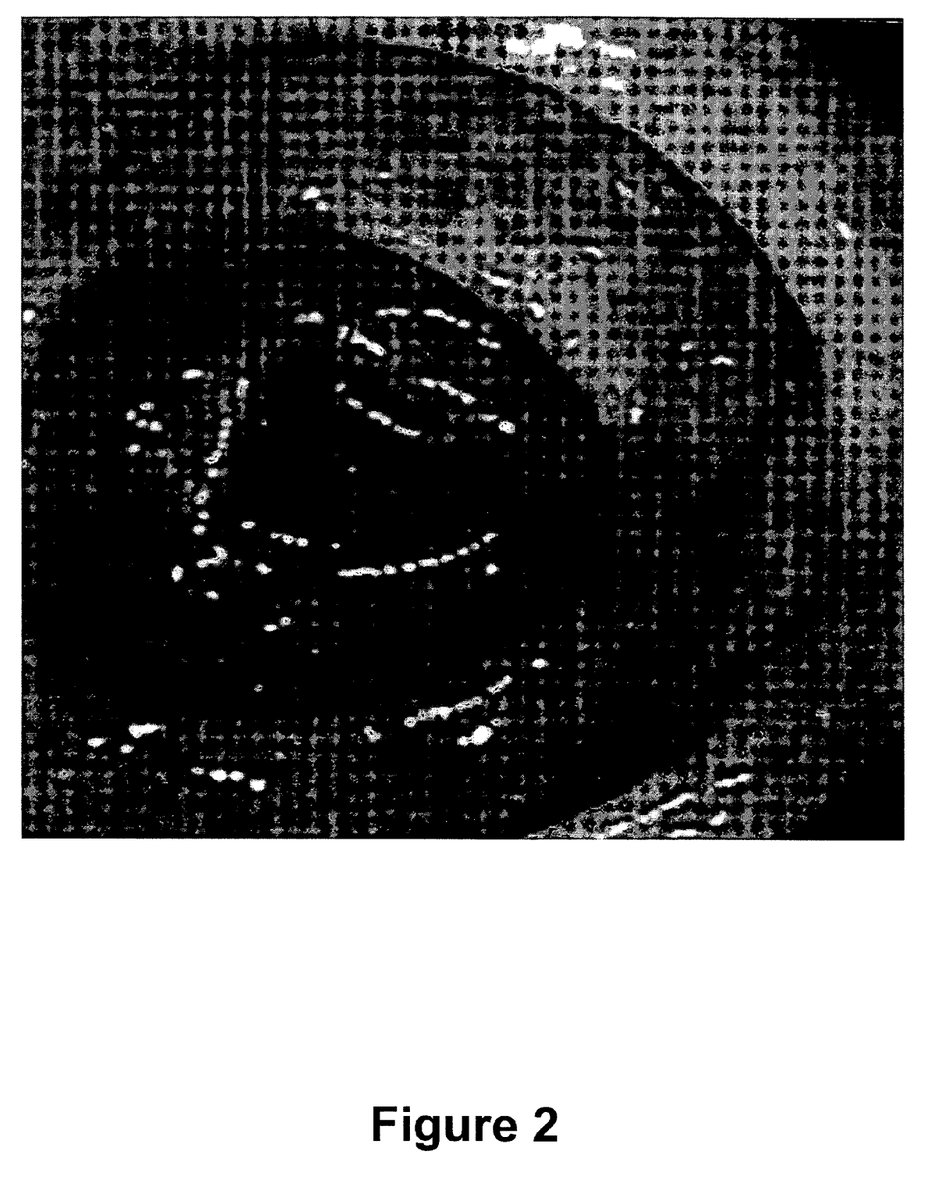
FIG. 2 shows that the composition of the invention, which contains a soluble, nonfermentable binder, leaves little or no residue after use for bowel preparation, thereby increasing visualization of the colon.

Any binder that is soluble, or soluble and nonfermentable, may be used in the present invention. However, binders that are fermentable, like any other fermentable ingredient, should only be used in embodiments where a spark would not be produced in the colon. A soluble, nonfermentable binder that may be used in the formulations of the invention includes, but is not limited to, polyethylene glycol (PEG). Applicants discovered that a purgative composition containing the soluble, nonfermentable binder PEG, leaves little or no residue after use for bowel preparation, thereby increasing visualization of the colon (FIG. 2). PEG is represented by the structural formula:

$HOCH_2(CH_2OCH_2)_mCH_2OH$, wherein m represents the average number of oxyethylene groups.

Any PEG polymer may be employed in the compositions contemplated herein. In one embodiment, the PEG polymers are solid at room temperature (i.e., 25° C.) and/or soluble in (or miscible with) water at room temperature. In one embodiment of the invention, the average molecular weight of the PEG polymer is at least 200, at least 400, at least 600, at least 1,000, at least 1540, at least 3000, at least 4,000, or at least 8,000. In one embodiment of the invention, the average molecular weight of the PEG polymer is from 7,000 to 9,000.

The amount of soluble and/or non-fermentable binder may vary depending on the desired characteristics of the solid dosage form and can be determined by one of ordinary skill in the art. In one embodiment of the invention, a PEG binder comprises 5-20%, in another embodiment 7.5-15%, and in an additional embodiment 10% by weight.

In one embodiment of the invention, the composition of the invention is free of insoluble binder or only contains levels of insoluble binder that do not impede the visualization of the colon.

Various purgatives are available commercially, and any available form of the material can be used in the practice of this invention. Purgatives that may be used in the invention include, but are not limited to, non-osmotic, osmotic, and bulk-forming purgatives. The invention may contain one purgative, more than one purgative from the same category, or more than one purgative from different categories may be used. Many purgatives may have more than one role or function, or may be classified in more than one group. Such classifications are descriptive only, and not intended to limit any use of a particular purgative.

In one embodiment of the invention, at least one osmotic purgative is used in the formulation of the invention. Osmotic purgatives act by increasing intestinal osmotic pressure thereby promoting retention of fluid within the bowel. Osmotic purgatives that may be included in the composition include salts, for example, magnesium citrate, magnesium chloride, magnesium hydroxide, magnesium phosphate, magnesium sulfate, magnesium tartrate, sodium phosphate, sodium tartrate, sodium sulfate, potassium tartrate, magnesium oxide, sodium sulfate, or salts thereof. Other examples of osmotic purgatives include glycerin, sorbitol, mannitol, lactitol, alcohol sugars, L-sugars, polyethylene glycol, and lactulose. However, purgatives that are fermentable should only be used in embodiments where a spark would not be produced in the colon.

In one embodiment of the invention, the at least one purgative is sodium phosphate or a salt thereof. In an additional embodiment of the invention, the at least one purgative is monobasic sodium phosphate, dibasic sodium phosphate, or tribasic sodium phosphate.

Salts according to the present invention may be used in a variety of forms, for example anhydrous or a hydrated form. It is also contemplated that a change in the form of a salt may increase or decrease its molecular weight. To account for any change in molecular weight, components of the purgative formulation and/or amounts of the purgative salts may be adjusted according to the knowledge of the person of ordinary skill in the art. In one embodiment of the invention, monobasic sodium phosphate is used in a monohydrate form. In another embodiment of the invention, dibasic sodium phosphate is used in an anhydrous form.

In one embodiment of the invention, the formulation of the invention comprises at least one non-osmotic purgative. Non-osmotic purgatives include prokinetic laxatives that stimulate the motility of the gastrointestinal tract, as well as stimulant laxatives that act by directly stimulating nerve endings in the colonic mucosa. Emollient laxatives and mucosal protectants may also be used in the invention. Examples of non-osmotic purgatives that may be used in the invention include, but are not limited to, mineral oil, aloe, bisacodyl, sodium picosulfate, casanthranol, cascara, castor oil, danthron, dehydrocholic acid, phenolphthalein, sennosides, docusate, bethanachol, colchicines, misoprostol, cisapride, norcisapride, paraffin, rhein, and tegaserod.

In one embodiment of the invention, the colonic purgative composition contains at least one osmotic purgative and at least one non-osmotic purgative.

In addition to at least one osmotic purgative and/or at least one non-osmotic purgative, the colonic purgative formulations of the invention may also comprise at least one bulk-forming purgative. Bulk-forming purgatives cause retention of fluid and an increase in fecal mass, resulting in stimulation of peristalsis. Bulk-forming laxatives may include various natural and semisynthetic polysaccharides, cellulose derivatives, or other substances that dissolve or swell in water to form an emollient gel or viscous solution that serves to maintain the feces soft and hydrated. Examples of bulk-forming purgatives that can be used in the invention include, but are not limited to, methylcellulose, sodium carboxymethyl cellulose, bran, psyllium, sterculia, and testa ispaghula.

2. Additional Optional Ingredients

Additional optional components may be included in the formulations of this invention to, for example, enhance the characteristics of the solid dosage form, maintain the integrity of particles of the active ingredient during the formulation process, and/or enhance the safety of the formulation. Any additional components may be compatible with the other ingredients in the formulations of the invention, in particular the active ingredients, and may not adversely affect the osmolarity of the formulations. Additional optional ingredients that may be used in the formulations of the invention include, for example, coatings, diluents, binders, glidants, lubricants, colors, disintegrants, flavors, sweeteners, polymers or waxes.

Lubricants, for example, may be included in the formulations of the invention. Such lubricants include, but are not limited to, magnesium stearate, potassium stearate, talc, stearic acid, sodium lauryl sulphate, and paraffin. In one embodiment of the invention, the colonic purgative formulation further comprises magnesium stearate. Lubricants serve to facilitate the manufacturing of a solid dosage form.

Additional suitable ingredients also include, but are not limited to, carriers, such as sodium citrate and dicalcium phosphate; fillers or extenders, such as stearates, silicas, gypsum, starches, lactose, sucrose, glucose, mannitol, talc, and silicic acid; binders, such as hydroxypropyl methylcellulose, hydroxymethyl-cellulose, alginates, gelatin, polyvinyl pyrrolidone, sucrose, and acacia; humectants, such as glycerol; disintegrating agents, such as agar, calcium carbonate, potato and tapioca starch, alginic acid, certain silicates, colloidal silicon dioxide, sodium starch glycolate, crospovidone, and sodium carbonate; solution retarding agents, such as paraffin; absorption accelerators, such as quaternary ammonium compounds; wetting agents, such as cetyl alcohol and glycerol monostearate; absorbents, such as kaolin and bentonite clay; stabilizers, such as fumaric acid; coloring agents; buffering agents; dispersing agents; preservatives; organic acids; and organic bases.

In one embodiment of the invention, an additional component in the formulations of the invention may function to maintain the electrolyte balance in a patient. For example, formulations of the invention may further comprise calcium, phosphate, potassium, magnesium, other anions, or salts thereof, which may normally be lost in diarrhea fluid.

Acidic or basic compounds may also be optionally added to the composition to adjust the pH of the compound or to alter the disintegration characteristics. Acidic or basic compounds that may be included in the formulations of the invention include, but are not limited to, sodium carbonate, sodium bicarbonate, sodium phosphate, calcium carbonate, magnesium hydroxide, potassium hydroxide, magnesium carbonate, and aluminum hydroxide.

The aforementioned ingredients are given as examples only and are not meant to include all possible choices. Additionally, many may have more than one role or function, or be classified in more than one group. Such classifications are descriptive only, and not intended to limit any use of a particular component.

To optimize the solid dosage formulations, components and amounts of the colonic purgative formulations of the invention may be adjusted according to the knowledge of the person of ordinary skill in the art. Sample ingredient ranges for a colonic purgative formulation example are provided in Table 1. Not all of the components are necessary, but are provided for illustration only. For example, it may not be necessary to have two distinct purgatives and it may also not be necessary to have a lubricant, such as magnesium stearate.

TABLE 1

Example Ingredient Ranges for a Colonic Purgative Composition

| Ingredient | Function | Qty % (w/w) |
| --- | --- | --- |
| Sodium Phosphate, Monobasic Active | Active | 45.00-75.00 |
| Sodium Phosphate, Dibasic Active | Active | 15.00-30.00 |
| PEG-8000 | Binder | 5.00-20.00 |
| Magnesium Stearate | Lubricant | 0.10-1.50 |

3. Administration and Dosing

The present invention also encompasses methods of using the colonic purgative formulations. The colonic purgative formulations of the invention produce a broad range of activities, depending on the dosage administered. The present invention encompasses methods of purging the colon comprising administering to at least one patient a colonic purgative formulation and allowing said formulation to purge the colon. The formulations of the invention may also be used at lower doses in order to regulate, soften or loosen the stool.

Thus, the present invention also encompasses methods of maintaining the elimination or increasing the elimination of feces in the bowel, comprising administering to at least one patient a colonic purgative formulation and promoting the elimination of feces in the bowel. The colonic purgative formulations of the invention may also be used to treat a patient with constipation. The constipation may be caused by a variety of factors including, but not limited to at least one of travel; change in daily routine; lack of exercise; immobility caused by injury, illness, or aging; dehydration; irritable bowel syndrome; pregnancy; diabetes; hypothyroidism; hypercalcemia; cancer of the colon or rectum; uterine prolapse; vaginal vault prolapse; rectal prolapse; scarring from surgery; injury of the colon or rectum; Parkinson's disease; multiple sclerosis; stroke; hemorrhoid or anal fissures; delaying bowel movements; anxiety; depression; eating disorders; and obsessive-compulsive disorder. The constipation may also be idiopathic, i.e. of unknown causation.

In another embodiment of the invention the composition of the invention is used to treat a patient suffering from, or susceptible to, constipation due to administration of a medication that causes constipation. A medication that may cause constipation includes, but is not limited to antacids that contain aluminum; antidepressants; blood pressure medications; calcium channel blockers; calcium supplements; chemotherapy medications; cold medicines; antihistamines; diuretics; iron supplements; medications for Parkinson's disease; lipid-lowering agents; pain medications; opiates; codeine; and tranquilizers.

One of skill in the art will recognize that the appropriate dosage of the colonic purgative compositions may vary depending on the individual being treated and the purpose. For example, the age, body weight, and medical history of the individual patient may affect the therapeutic efficacy of the therapy. Further, a lower dosage of the composition may be needed to produce a mild catharsis, while complete purgation may require a higher dose. A competent physician can consider these factors and adjust the dosing regimen to ensure the dose is achieving the desired therapeutic outcome without undue experimentation. It is also noted that the clinician and/or treating physician will know how and when to interrupt, adjust, and/or terminate therapy in conjunction with individual patient response. Dosages also depend on the strength of the particular purgative(s) chosen for the formulation.

In one embodiment of the invention, the total dosage is administered in at least one application period. In an additional embodiment of the invention, the total dosage is administered in two or more separate application periods, or separate doses.

The dose of the colonic purgative formulations may vary. For example, a lower dose of a colonic purgative formulation of the invention may be needed to produce a mild catharsis, while complete purgation may require a higher dose. A total daily dosage used for mild catharsis, for example, can range from 1 g to 30 g of a purgative. For example, in general, a total daily dosage of a purgative, such as sodium phosphate, in formulations of the present invention ranges from 1 to 30 g, 2 to 25 g, 3 to 20 g, 4 to 18 g, 5 to 16 g, 6 to 14 g, or 8 to 12 g. A total daily dosage may be formulated to contain 1, 2, 4, 6, 8, 10, 12, 14, 16, 18, 20, 22, 24, 26, 28, or 30 g of a purgative, such as sodium phosphate. Additional doses of the colonic purgative formulation may be necessary to produce the desired therapeutic effect. In one embodiment of the invention, the total daily dosage is administered every 24 hours until the desired therapeutic effects are reached.

A higher dose of a colonic purgative formulation of the invention may be needed to produce a complete purgation of the colon. A total dosage used for complete purgation, for example, can range from 20 g to 100 g of a purgative, optionally provided over a period of time of up to 24 hours. For example, in general, a total daily dosage of a purgative, such as sodium phosphate, in formulations of the present invention may range from 20 to 100 g, 30 to 90 g, 40 to 80 g, or 50 to 70 g. A dose may be formulated to contain 20, 30, 40, 50, 60, 70, 80, 90, or 100 g of a purgative, such as sodium phosphate.

Optionally, in both the laxative and complete purgative embodiments, the total daily dosage may be separated into divided doses. In one embodiment of the invention, the total daily dosage is divided into two doses, separated by a period of up to 24 hours. For instance, a total daily dosage of 60 g of a purgative, such as sodium phosphate, may be divided into two doses of 30 g each. One dose of 30 g may be administered in the evening before a colon procedure, while the second dose of 30 g may be administered in the morning, 3 to 5 hours before the colon procedure. In another embodiment of the invention, the total daily dose is divided into three, four, or more doses.

In one embodiment of the invention, the addition of one or more purgatives to the composition, for example a colonic purgative composition comprising sodium phosphate and bisacodyl, may lower the amount of active ingredient in each dose, the number of doses, the administration time, and/or the number of tablets administered in a dose.

In one embodiment of the invention, the colonic purgative formulation is in an easily administered, solid dosage form. Solid dosage forms include, for example, a tablet, capsule, or caplet. The dosage form may be coated or encapsulated. In one embodiment of the invention, the colonic purgative formulation is in the form of a tablet. The number of tablets administered in a dose may vary depending on the desired effect and on the amount of active ingredient in each solid dosage form. Clear liquids may be taken with each dose.

A colonic purgative composition of the invention may be part of a kit. In one embodiment of the invention, the kit further comprises materials to assist in the administration of the composition, for instance a cup. In another embodiment of the invention, the kit further comprises compositions that assist in Taxation or complete purgation. Additional compositions that may be included in a kit with the colonic purgative compositions of the invention include, but are not limited to, at least one non-osmotic purgative, osmotic purgative, and/or bulk-forming laxative. In one embodiment of the invention, the kit comprises a colonic purgative composition of the invention and a composition containing bisacodyl.

A colonic purgative composition of the invention may be administered by various routes. In one embodiment of the invention, the purgative composition is administered orally. In an additional embodiment of the invention, the purgative composition is administered through a tube, for instance a feeding tube or nasogastric tube.

The colonic purgative formulations of the invention may be manufactured in a variety of ways. In one embodiment of the invention, the formulations may be produced using a direct-compression or hot-melt process. In an additional embodiment of the invention, a process of producing a colonic purgative formulation comprises mixing the components, warming the mixture to the melting point of the polyethylene glycol, and compressing the mixture into tablets. In the hot melt process, for instance, the ingredients may be mixed in a high-shear mixer equipped with a jacketed mixing bowl. The blend may be warmed up to the melting point of PEG during mixing and cooling down when the end-point is reached. The blend may be cooled down overnight, milled, lubricated, and compressed into tablets. One of ordinary skill in the art will recognize methods of varying the manufacturing process to optimize the dosage form or increase the product amount for large scale manufacturing.

C. EXAMPLES

The following examples are offered for illustrative purposes only.

Example 1

Preparation and Use of Colonic Purgative Formulations Containing an Insoluble Binder Two colonic purgative formulations, comprising the components set forth in Table 2, were produced by milling and blending, followed by direct compression.

TABLE 2

Prior Art Colonic Purgative Compositions Containing an Insoluble Binder

| Ingredient | Function | Diacol ® Qty % (w/w) | Visicol ® Qty % (w/w) |
|---|---|---|---|
| Sodium Phosphate, Monobasic Active | Active | 55.10 | 62.44 |
| Sodium Phosphate, Dibasic Active | Active | 19.90 | 22.55 |
| Microcrystalline Cellulose | Binder | 23.00 | 13.00 |
| Colloidal Silicone Dioxide | Diluent | 0.50 | 0.50 |
| Magnesium Stearate | Lubricant | 1.50 | 1.50 |
| Total | | 100 | 100 |

The target weight of each Diacol® tablet (InKine Pharmaceutical Company, Blue Bell, Pa.) was 2000.0 mg, which was consistently achieved by the manufacturing process. The target weight of each Visicol® tablet (InKine Pharmaceutical Company, Blue Bell, Pa.) was 1764.8.0 mg, which was consistently achieved by the manufacturing process. Physical testing of both formulations revealed that the tablets exhibited an appropriate strength, hardness, and disintegration time.

Visicol® tablets were administered to humans in two, twenty tablet doses. One dose was administered the night before the colonoscopy procedure and the second dose was administered in the morning, 3 to 5 hours before the procedure. Colonoscopy revealed the presence of the binder, MCC, in the colon of patients. As shown in FIG. 1, MCC leaves a white powdery substance in the colon after use for bowel preparation, which significantly impairs visualization of the colon.

Example 2

Preparation of a Colonic Purgative Formulation Containing a Soluble, Nonfermentable Binder A colonic purgative formulation comprising the components set forth in Table 3, was produced using a hot melt process via high-shear granulation followed by milling, lubrication, and compression.

TABLE 3

Colonic Purgative Composition Containing a Soluble, Nonfermentable Binder

| Ingredient | Function | Qty % (w/w) | Qty/Dosage Form (mg) | Qty/Batch (kg) |
|---|---|---|---|---|
| Sodium Phosphate, Monobasic Active | Active | 65.75 | 1102.0 | 295.9 |
| Sodium Phosphate, Dibasic Active | Active | 23.75 | 398.0 | 106.9 |
| PEG-8000 | Binder | 10.00 | 167.6 | 45.0 |
| Magnesium Stearate | Lubricant | 0.50 | 8.4 | 2.26 |
| Total | | 100 | 1676.0 | 450.06 |

Specifically, sodium phosphate monobasic monohydrate (295.9 kg) was passed through a sieve equipped with a 10 mesh stainless steel screen. Sodium phosphate dibasic anhydrous (106.9 kg) and polyethylene glycol 8000 (45.0 kg) were each passed through a sieve equipped with a 20 mesh stainless steel screen. The sieved sodium phosphate monobasic monohydrate, sodium phosphate dibasic anhydrous, and polyethylene glycol 8000 were loaded into a 250 L bin and blended for 23 minutes±60 seconds at 12 rpm in a bin blender. The blended mixture was then transferred into suitable double poly-lined containers and milled through a cone mill, equipped with a stainless steel screen, at an impeller speed of 1400-1500 rpm. The milled mixture was then transferred back to the bin blender and further blended for 45 minutes±60 seconds at 12 rpm.

After the blending was complete, the materials were discharged into double poly-lined containers and divided into three sections. The lower jacket temperature on a mixer was set to 59° C., the upper jacket was turned on, and the heating water began circulating through the jacketed mixing bowl. When the lower jacket temperature reached 59° C.-60° C., the first section of blended materials was loaded into the mixing bowl of the mixer and the impeller speed was set at 30 rpm (with the granulator not running). The lower jacket temperature was then set to 66° C. and the impeller speed at 50 rpm. When the product temperature reached 40° C.-41° C., the impeller speed was increased to 100 rpm. When the product temperature reached 52° C., the granulator was set to speed 1 (slow) and the lower jacket temperature was set to 58° C. When the product temperature reached 54° C.-55° C., the granulation process was stopped. The lower jacket temperature was reduced to 20° C., the upper jacket was turned off, and the impeller speed was decreased to 10 rpm. The mixture was cooled until the product temperature reached 52° C. The granulation was then discharged into double poly-lined containers and stored in a closed container at room temperature overnight. The process detailed above was repeated for divided sections two and three of the blended materials.

The next day, the temperature of the granulation was checked to ensure that it was less than 30° C. The granulation was then milled through the cone mill, equipped with a stainless steel screen, at an impeller speed of 1400-1500 rpm. The milled granulation was loaded into a 1200 L bin and blended for 23 minutes±30 seconds at 12 rpm in a bin blender. Magnesium stearate (2.26 kg) was passed through a 30 mesh stainless steel hand screen and then added to the milled granulation in the 1200 L bin. The magnesium stearate was blended with the milled granulation for 10 minutes±30 seconds at 12 rpm in the bin blender. The blended mixture was then compressed into tablets using a tablet press and dedusted using a tablet deduster.

The target weight of each tablet was 1676.0 mg, which was consistently achieved by the manufacturing process. Physical testing of the tablet revealed that the tablet formulation exhibited an appropriate strength, hardness, and disintegration time. Surprisingly, the INKP-102 tablet could be formulated successfully as a smaller tablet than the prior art compositions, Diacol® and Visicol®, even though the same amount of active ingredient (1102 mg sodium phosphate monobasic monohydrate and 398 mg sodium phosphate dibasic anhydrous) was used in each of the three compositions (Table 4). This surprising result is very beneficial as the improved formulation is more tolerable to patients, allowing them to more easily administer the active ingredients. Further, the disintegration time of the INKP-102 tablet is decreased, resulting in a more rapid response to the colonic purgative composition. Additionally, this decrease in disintegration time cannot be accounted for merely by the reduced size of the tablet, as there is a steeper decline in disintegration time compared to tablet size. This more rapid response would be especially beneficial whether a patient administered the composition of the invention to treat constipation or to completely purge the colon.

TABLE 4

Colonic Purgative Composition Containing a Soluble, Nonfermentable Binder

| | Diacol ® | Visicol ® | INKP-102 |
|---|---|---|---|
| Amount of Binder | 23% | 13% | 10% |
| Binder | MCC | MCC | PEG |
| Tablet Dimensions | 0.950 × 0.406 in. thickness: 6.72 mm | 0.850 × 0.352 in. thickness: 7.12 mm | 0.750 × 0.40 in. thickness: 6.86 mm |
| Tablet Properties | large,_dry__, and difficult to swallow | large,_dry__, and difficult to swallow | smaller, waxy, and easy to swallow |
| Weight (mg) | 2000.0 | 1764.8 | 1676.0 |
| Disintegration Time | approx. 31 minutes | approx. 25 minutes | approx. 11 minutes |

Example 3

Preparation of a Colonic Purgative Formulation Containing a Soluble, Nonfermentable Binder A colonic purgative formulation, comprising the components set forth in Table 5, is produced using a hot melt process via high-shear granulation followed by milling, lubrication, and compression.

TABLE 5

Colonic Purgative Composition Containing a Soluble, Nonfermentable Binder

| Ingredient | Function | Qty % (w/w) |
|---|---|---|
| Sodium Phosphate, Monobasic Active | Active | 65.73% |
| Sodium Phosphate, Dibasic Active | Active | 23.74% |
| Bisacodyl | Active | 0.03% |
| PEG-8000 | Binder | 10.00 |
| Magnesium Stearate | Lubricant | 0.50 |
| Total | | 100 |

Physical testing of the tablet formulation includes weight variation, strength, hardness, and disintegration time. It is expected that a tablet formulated according to the above parameters will have appropriate physical properties.

Example 4

A Colonic Purgative Composition to Purge the Colon

A patient undergoing a surgical or diagnostic procedure involving the colon is administered 40 tablets of a colonic purgative composition, such as the composition described in Example 2 or 3. The evening before the surgical or diagnostic procedure, 3 tablets are taken with at least 8 ounces of clear liquids every 15 minutes (the last dose will be 2 tablets) for a total of 20 tablets. Optionally, the day of the colonoscopy procedure, (starting 3 to 5 hours before the procedure) 3 tablets are taken with at least 8 ounces of clear liquids every 15 minutes (the last dose will be 2 tablets) for a total of 20 tablets. It is expected that the results of such treatment will provide an adequately cleansed bowel, demonstrate little or no residue that impairs visual inspection of the colon, and is tolerable to the patient both in its palatability and side effect profile.

Example 5

A Colonic Purgative Composition Containing an Osmotic and Non-Osmotic Purgative to Purge the Colon A colonic purgative formulation of the invention may also be administered in a single application or dose. A patient undergoing a surgical or diagnostic procedure involving the colon is administered 20 tablets of a colonic purgative composition, such as the composition described in Example 3. The evening before the surgical or diagnostic procedure, 3 tablets are taken with at least 8 ounces of clear liquids every 15 minutes (the last dose will be 2 tablets) for a total of 20 tablets. It is expected that the results of such treatment will provide an adequately cleansed bowel, demonstrate little or no residue that impairs visual inspection of the colon, and is tolerable to the patient both in its palatability and side effect profile. Further, it is expected that no morning dose will be required to obtain quality cleansing of the bowel.

Example 6

A Colonic Purgative Composition to Treat Constipation

A patient with constipation is treated with a colonic purgative composition, such as the composition described in Example 2 or 3. The composition is administered in a total daily dose of 3 to 18 g, which is given over a period of up to 30 minutes. The dose may be repeated daily. It is expected that the results of such treatment will facilitate the passage of feces and promote elimination, by loosening or softening of the stool and/or the promotion of peristalsis due to increased amounts of water in the colon. It is beneficial to be able to use the same dual function composition for complete purgation and laxation.

Example 7

Colon Cleansing Efficacy of INKP-102

The primary objective of this study was to compare, by direct visualization, the colon cleansing efficacy of a composition of one embodiment of the invention (See Table 3; hereinafter "INKP-102") versus the marketed Visicol® tablets (See Table 2; InKine Pharmaceutical Company, Blue Bell, Pa.) in patients undergoing colonoscopy. In addition, the safety of the INKP-102 composition was evaluated. The components of INKP-102 (1676 mg tablet) were as set forth in Table 3 above. Visicol® tablets were comprised of the same amount of active ingredient as INKP-102 (1102 mg sodium phosphate monobasic monohydrate and 398 mg sodium phosphate dibasic anhydrous). However, the inert ingredients of Visicol® tablets included MCC, colloidal silicon dioxide, and magnesium stearate, as set forth in Table 2 above.

Treatments

Patients were randomly assigned (approximately 30 patients per group) to one of the seven treatment arms (Arms A-G). Each arm had a unique dosing regimen, as described in Table 6. Patients received either Visicol® Tablets (Arm A; 60 g sodium phosphate dose, as label recommends) or one of 6 dosing regimens of INKP-102 (Arms B-G; 42-60 g of sodium phosphate). There were two scheduled visits: a screening visit (Visit 0) and the colonoscopy visit (Visit 1). The screening visit took place up to 14 days prior to Visit 1. Patients self-administered the trial medication.

TABLE 6

Dosing Instructions for Treatment Arms A-G

| Treatment Arm | Dosing Instructions |
|---|---|
| A | 40 Visicol ® Tablets (60 g sodium phosphate) by mouth as follows: 20 tablets over 1.5 hours beginning at 6 p.m. the evening before colonoscopy and 20 tablets over 1.5 hours beginning 3 to 5 hours before colonoscopy, with tablets taken 3 at a time every 15 minutes with at least 8 oz. of clear liquid. (As recommended in the approved labeling) |
| B | 40 INKP-102 tablets (60 g sodium phosphate) by mouth as follows: 20 tablets over 1.5 hours beginning at 6 p.m. the evening before colonoscopy and 20 tablets over 1.5 hours beginning 3 to 5 hours before colonoscopy, with tablets taken 3 at a time every 15 minutes with at least 8 oz. of clear liquid. |
| C | 40 INKP-102 tablets (60 g sodium phosphate) by mouth as follows: 20 tablets over 1 hour beginning at 6 p.m. the evening before colonoscopy and 20 tablets over 1 hour beginning 3 to 5 hours before colonoscopy, with tablets taken 4 at a time every 15 minutes with at least 8 oz. of clear liquid. |
| D | 32 INKP-102 tablets (48 g sodium phosphate) by mouth as follows: 20 tablets over 1 hour beginning at 6 p.m. the evening before colonoscopy and 12 tablets over a half-hour period beginning at 10 p.m. the same evening, with tablets taken 4 at a time every 15 minutes with at least 8 oz. of clear liquid. No tablets are taken on the day of colonoscopy. |

TABLE 6-continued

Dosing Instructions for Treatment Arms A-G

| Treatment Arm | Dosing Instructions |
|---|---|
| E | 32 INKP-102 tablets (48 g sodium phosphate) by mouth as follows: 20 tablets over 1 hour beginning at 6 p.m. the evening before colonoscopy and 12 tablets over a half-hour period the next day beginning 3 to 5 hours before colonoscopy, with tablets taken 4 at a time every 15 minutes with at least 8 oz. of clear liquid. |
| F | 28 INKP-102 tablets (42 g sodium phosphate) by mouth as follows: 20 tablets taken over 1 hour beginning at 6 p.m. the evening before colonoscopy and 8 tablets taken over 15 minutes beginning at 9 p.m. the same evening, with tablets taken 4 at a time every 15 minutes with at least 8 oz. of clear liquid. |
| G | 28 INKP-102 tablets (42 g sodium phosphate) by mouth as follows: 20 tablets beginning at 6 p.m. the evening before colonoscopy and 8 tablets the next day beginning 3 to 5 hours before colonoscopy, with tablets taken 4 at a time every 15 minutes with at least 8 oz. of clear liquid. |

Efficacy

Two hundred and fourteen patients took at least one dose of the study drug and completed their colonoscopy. Unless otherwise noted, this population ("All-Assessed" population) was evaluated for treatment efficacy. Patients that completed at least 90% of their designated study regimen, were not known to have dosed >2 hours outside of the recommended time frame, and had their colonoscopy, were designated as the "Per Protocol" population and numbered 192.

The primary objective of the study was to evaluate the colon cleansing efficacy of INKP-102 compared with Visicol® tablets in patients undergoing colonoscopy. The overall quality of the colonic cleansing was evaluated based on (1) the amount of stool (liquid, semisolid, or solid) observed during the procedure and (2) the amount of "colonic contents" (including all liquid, semisolid, and solid material in the lumen of the colon) observed during the procedure rather than only "stool." Both the "stool" and "colonic contents" endpoints were based on endoscopist assessment using the following 4-point scale:

| 1 = Excellent: | >90% of mucosa seen, mostly liquid colonic contents (or stool), minimal suctioning needed for adequate visualization. |
|---|---|
| 2 = Good: | >90% of mucosa seen, mostly liquid colonic contents (or stool), significant suctioning needed for adequate visualization. |
| 3 = Fair: | >90% of mucosa seen, mixture of liquid and semisolid colonic contents (or stool), could be suctioned and/or washed. |
| 4 = Inadequate: | <90% of mucosa seen, mixture of solid and semisolid colonic contents (or stool), which could not be suctioned or washed. |

Using this 4-point scale, endoscopists assessed the patients' colons overall, and also specifically assessed patients' ascending colons, where MCC residue especially impairs visualization of the colon.

Tables 7a and 7b display the results of endoscopist assessment of "colonic contents" overall and in the ascending colon, respectively, in the "All-Assessed" population. Comparison of Visicol® versus INKP-102 treatments revealed that mean overall colonic contents scores were significantly better with INKP-102 dosages (Arms B, C, and E) than with Visicol® ($P<0.05$; Arm A). Similarly, assessment of colonic contents in the ascending colon revealed that INKP-102 treatment with Arms B, C, and E resulted in significantly better mean colonic contents scores than with Visicol® treatment ($P<0.05$; Arm A).

Surprisingly, treatment with Arm E resulted in these significantly better mean colonic contents scores, even though the amount of sodium phosphate (48 g) was lower than the sodium phosphate content of the marketed Visicol® (60 g). In addition, treatment Arms D, F, and G performed as well as the marketed Visicol® (no statistically significant difference), even though the amount of sodium phosphate (48 g, 42 g, and 42 g, respectively) was lower than the sodium phosphate content of the marketed Visicol® (60 g). This surprising result is very beneficial as the improved formulation allows patients to use a lower dose of active ingredients to achieve the same result. It is expected that the same will hold true for laxative uses of the composition. Because the dosing regimens of treatment Arms D and F only involve an evening dose, they may be more preferable to patients who do not want to get up early before a procedure to complete a dosing regimen and more preferable to anesthesiologists who require that the patient receive nothing by mouth on the morning of the procedure.

Analysis of the smaller "Per Protocol" population yielded similar results. Additionally, in the per protocol group, improvement in "colonic content" overall and in the ascending colon upon INKP-102 Arm G treatment versus Arm A Visicol® treatment reached statistical significance ($P<0.0346$). Surprisingly, treatment with Arm G resulted in these significantly better mean colonic contents scores, even though the amount of sodium phosphate (42 g) was lower than the sodium phosphate content of the marketed Visicol® (60 g).

TABLE 7a

Overall Colonic Contents in the "All-Assessed" Population

| | Visicol ® | INKP-102 Treatment Groups | | | | | | |
|---|---|---|---|---|---|---|---|---|
| | 40 Tabs (60 g) | 40 Tabs (60 g) | | 32 Tabs (48 g) | | 28 Tabs (42 g) | | |
| | A 3 tabs split (n = 29) | B 3 tabs split (n = 32) | C 4 tabs split (n = 29) | D 4 tabs (n = 30) | E 4 tabs split (n = 33) | F 4 tabs (n = 32) | G 4 tabs split (n = 29) | All patients (n = 214) |
| Parameter | n (%) | n (%) | n (%) | n (%) | n (%) | n (%) | n (%) | n (%) |
| Excellent | 14 (48) | 24 (75) | 22 (76) | 18 (60) | 26 (79) | 15 (47) | 22 (76) | 141 (66) |
| Good | 11 (38) | 7 (22) | 7 (24) | 9 (30) | 6 (18) | 8 (25) | 4 (14) | 52 (24) |

TABLE 7a-continued

Overall Colonic Contents in the "All-Assessed" Population

| | Visicol ® | INKP-102 Treatment Groups | | | | | | |
|---|---|---|---|---|---|---|---|---|
| | 40 Tabs (60 g) | 40 Tabs (60 g) | | 32 Tabs (48 g) | | 28 Tabs (42 g) | | |
| Parameter | A 3 tabs split (n = 29) n (%) | B 3 tabs split (n = 32) n (%) | C 4 tabs split (n = 29) n (%) | D 4 tabs (n = 30) n (%) | E 4 tabs split (n = 33) n (%) | F 4 tabs (n = 32) n (%) | G 4 tabs split (n = 29) n (%) | All patients (n = 214) n (%) |
| Fair | 4 (14) | 1 (3) | 0 (0) | 1 (3) | 1 (3) | 5 (16) | 2 (7) | 14 (7) |
| Inadequate | 0 (0) | 0 (0) | 0 (0) | 2 (7) | 0 (0) | 4 (13) | 1 (3) | 7 (3) |
| Mean | 1.66 | 1.28 | 1.24 | 1.57 | 1.24 | 1.94 | 1.38 | 1.47 |
| Std. Dev. | 0.72 | 0.52 | 0.44 | 0.86 | 0.50 | 1.08 | 0.78 | 0.76 |
| P-value* | N/A | 0.0472† | 0.0322† | 0.6422 | 0.0275† | 0.1332 | 0.1519 | N/A |

*P-values were obtained using an ANOVA with factor treatment used to compare the means between INKP-102 and Visicol ® groups.
†Statistically significant (at the 0.05 level)

TABLE 7b

Ascending Colon Colonic Contents in the "All-Assessed" Population

| | Visicol ® | INKP-102 Treatment Groups | | | | | | |
|---|---|---|---|---|---|---|---|---|
| | 40 Tabs (60 g) | 40 Tabs (60 g) | | 32 Tabs (48 g) | | 28 Tabs (42 g) | | |
| Parameter | A 3 tabs split (n = 28) n (%) | B 3 tabs split (n = 32) n (%) | C 4 tabs split (n = 28) n (%) | D 4 tabs (n = 29) n (%) | E 4 tabs split (n = 33) n (%) | F 4 tabs (n = 32) n (%) | G 4 tabs split (n = 29) n (%) | All patients (n = 211) n (%) |
| Excellent | 11 (38) | 24 (75) | 21 (72) | 15 (50) | 27 (82) | 15 (47) | 20 (69) | 133 (62) |
| Good | 12 (41) | 7 (22) | 7 (24) | 5 (17) | 6 (18) | 7 (22) | 6 (21) | 50 (23) |
| Fair | 5 (17) | 1 (3) | 0 (0) | 8 (27) | 0 (0) | 6 (19) | 2 (7) | 22 (10) |
| Inadequate | 0 (0) | 0 (0) | 0 (0) | 1 (3) | 0 (0) | 4 (13) | 1 (3) | 6 (3) |
| Mean | 1.79 | 1.28 | 1.25 | 1.83 | 1.18 | 1.97 | 1.45 | 1.53 |
| Std. Dev. | 0.74 | 0.52 | 0.44 | 0.97 | 0.39 | 1.09 | 0.78 | 0.79 |
| P-value* | N/A | 0.0097† | 0.0078† | 0.8325 | 0.0019† | 0.3444 | 0.0894 | N/A |

*P-values were obtained using an ANOVA with factor treatment used to compare the means between INKP-102 and Visicol ® groups.
†Statistically significant (at the 0.05 level)

Tables 8a and 8b display the results of endoscopist assessment of "stool" overall and in the ascending colon, respectively, in the "All-Assessed" population. Mean "stool" endpoint scores overall and in the ascending colon generally favored INKP-102 dose groups over Visicol®. However, only INKP-102 Arm E showed statistically significant improvement over Visicol®, and only in the ascending colon. In contrast, treatment with Visicol® was statistically superior to INKP-102 Arm F in the ANOVA comparisons of means for both the overall "stool" score and ascending colon stool scores. These results were comparable in the analyses of the Per Protocol population.

Surprisingly, treatment with Arm E resulted in the significantly better mean stool score in the ascending colon (P<0.05) and a similar mean stool score in the overall colon (no statistically significant difference), even though the amount of sodium phosphate (48 g) was lower than the sodium phosphate content of the Arm A Visicol® (60 g). Further, treatment with Arms D and G performed as well as the marketed Visicol®, even though the amount of sodium phosphate (48 g and 42 g, respectively) was lower than the sodium phosphate content of Arm A Visicol® (60 g). This surprising result is very beneficial as the improved formulation allows patients to use a lower dose of active ingredients to achieve the same result. It is expected that the same will hold true for laxative uses of the composition. Because the dosing regimen of treatment Arm D only involves an evening dose, it may be more preferable to patients who do not want to get up early before a procedure to complete a dosing regimen and more preferable to anesthesiologists who require that the patient receive nothing by mouth on the morning of the procedure.

TABLE 8a

Overall Stool in the "All-Assessed" Population

| | Visicol® | INKP-102 Treatment Groups | | | | | | |
|---|---|---|---|---|---|---|---|---|
| | 40 Tabs (60 g) | 40 Tabs (60 g) | | 32 Tabs (48 g) | | 28 Tabs (42 g) | | |
| | A 3 tabs split (n = 29) n (%) | B 3 tabs split (n = 32) n (%) | C 4 tabs split (n = 29) n (%) | D 4 tabs (n = 30) n (%) | E 4 tabs split (n = 33) n (%) | F 4 tabs (n = 32) n (%) | G 4 tabs split (n = 29) n (%) | All patients (n = 214) n (%) |
| Parameter | | | | | | | | |
| Excellent | 20 (69) | 28 (88) | 24 (83) | 19 (63) | 29 (88) | 16 (50) | 24 (83) | 160 (75) |
| Good | 6 (21) | 3 (9) | 5 (17) | 7 (23) | 4 (12) | 8 (25) | 2 (7) | 35 (16) |
| Fair | 3 (10) | 1 (3) | 0 (0) | 2 (7) | 0 (0) | 5 (16) | 2 (7) | 13 (6) |
| Inadequate | 0 (0) | 0 (0) | 0 (0) | 2 (7) | 0 (0) | 3 (9) | 1 (3) | 6 (3) |
| Mean | 1.41 | 1.16 | 1.17 | 1.57 | 1.12 | 1.84 | 1.31 | 1.37 |
| Std. Dev. | 0.68 | 0.45 | 0.38 | 0.90 | 0.33 | 1.02 | 0.76 | 0.72 |
| P-value* | N/A | 0.1473 | 0.1846 | 0.3962 | 0.0975 | 0.0160[†] | 0.5690 | N/A |

*P-values were obtained using an ANOVA with factor treatment used to compare the means between INKP-102 and Visicol® groups.
[†]Statistically significant (at the 0.05 level)

TABLE 8b

Ascending Colon Stool in the "All-Assessed" Population

| | Visicol® | INKP-102 Treatment Groups | | | | | | |
|---|---|---|---|---|---|---|---|---|
| | 40 Tabs (60 g) | 40 Tabs (60 g) | | 32 Tabs (48 g) | | 28 Tabs (42 g) | | |
| | A 3 tabs split (n = 29) n (%) | B 3 tabs split (n = 32) n (%) | C 4 tabs split (n = 29) n (%) | D 4 tabs (n = 30) n (%) | E 4 tabs split (n = 33) n (%) | F 4 tabs (n = 32) n (%) | G 4 tabs split (n = 29) n (%) | All patients (n = 214) n (%) |
| Parameter | | | | | | | | |
| Excellent | 16 (55) | 27 (84) | 23 (79) | 17 (57) | 30 (91) | 15 (47) | 22 (76) | 150 (70) |
| Good | 7 (24) | 4 (13) | 5 (17) | 3 (10) | 3 (9) | 8 (25) | 4 (14) | 34 (16) |
| Fair | 4 (14) | 1 (3) | 0 (0) | 8 (27) | 0 (0) | 5 (16) | 2 (7) | 20 (9) |
| Inadequate | 0 (0) | 0 (0) | 0 (0) | 1 (3) | 0 (0) | 4 (13) | 1 (3) | 6 (3) |
| Mean | 1.56 | 1.19 | 1.18 | 1.76 | 1.09 | 1.94 | 1.38 | 1.44 |
| Std. Dev. | 0.75 | 0.47 | 0.39 | 0.99 | 0.29 | 1.08 | 0.78 | 0.78 |
| P-value* | N/A | 0.0553 | 0.0572 | 0.3000 | 0.0151[†] | 0.0468[†] | 0.3682 | N/A |

*P-values were obtained using an ANOVA with factor treatment used to compare the means between INKP-102 and Visicol® groups.
[†]Statistically significant (at the 0.05 level)

Analysis of the two efficacy endpoints together demonstrates that the INKP-102 treatment arms were generally rated higher than the Visicol® treatment arm in the "colonic contents" efficacy endpoint versus the "stool" efficacy endpoint. These results indicate that components of the colon other than stool, such as microcrystalline cellulose (MCC), do not hinder visualization of the colon after INKP-102 treatment to the extent that Visicol® treatment hinders visualization. At the same time, INKP-102 is able to effectively purge the colon of stool in liquid, semisolid, or solid form.

Both "colonic contents" and "stool" efficacy endpoints were also analyzed by dividing the 4-point assessment scale into "responder" and "non-responder" categories. For each assessment, a patient was considered to be a "responder" if colon cleansing was rated as "excellent" or "good" and a "non-responder" if colon cleansing was rated as "fair" or "inadequate. Table 9a and 9b display the number of "responders" and "non-responders" to the various treatment arms using a "colonic contents" and "stool" endpoint, respectively, in the "All-Assessed" population.

TABLE 9a

Colonic Cleansing (Colonic Contents) Responder Rates in the "All-Assessed" Population

| Parameter | Visicol® 40 Tabs (60 g) A 3 tabs split (n = 29) n (%) | INKP-102 Treatment Groups 40 Tabs (60 g) | | 32 Tabs (48 g) | | 28 Tabs (42 g) | | All patients (n = 214) n (%) |
|---|---|---|---|---|---|---|---|---|
| | | B 3 tabs split (n = 32) n (%) | C 4 tabs split (n = 29) n (%) | D 4 tabs (n = 30) n (%) | E 4 tabs split (n = 33) n (%) | F 4 tabs (n = 32) n (%) | G 4 tabs split (n = 29) n (%) | |
| Responder | 25 (86) | 31 (97) | 29 (100) | 27 (90) | 32 (97) | 23 (72) | 26 (90) | 193 (90) |
| Non-responder | 4 (14) | 1 (3) | 0 (0) | 3 (10) | 1 (3) | 9 (28) | 3 (10) | 21 (10) |
| P-value | N/A | 0.1816 | 0.1120 | 0.7065 | 0.1762 | 0.2192 | >0.9999 | N/A |

*P-values were obtained using a Fisher's Exact test to compare the response rates between Treatment arm A and the other Treatment arms (B-G).

TABLE 9b

Colonic Cleansing (Stool) Responder Rates in the "All-Assessed" Population

| Parameter | Visicol® 40 Tabs (60 g) A 3 tabs split (n = 29) n (%) | INKP-102 Treatment Groups 40 Tabs (60 g) | | 32 Tabs (48 g) | | 28 Tabs (42 g) | | All patients (n = 214) n (%) |
|---|---|---|---|---|---|---|---|---|
| | | B 3 tabs split (n = 32) n (%) | C 4 tabs split (n = 29) n (%) | D 4 tabs (n = 30) n (%) | E 4 tabs split (n = 33) n (%) | F 4 tabs (n = 32) n (%) | G 4 tabs split (n = 29) n (%) | |
| Responder | 26 (90) | 31 (97) | 29 (100) | 26 (87) | 33 (100) | 24 (75) | 26 (90) | 195 (91) |
| Non-responder | 3 (10) | 1 (3) | 0 (0) | 4 (13) | 0 (0) | 8 (25) | 3 (10) | 19 (9) |
| P-value* | N/A | 0.3385 | 0.2368 | >0.9999 | 0.0966 | 0.1884 | >0.9999 | N/A |

*P-values were obtained using a Fisher's Exact test to compare the response rates between Treatment arm A and the other Treatment arms (B-G).

The results indicate that treatment arms B, C, and E had higher responder rates among all treatment groups, and had lower or negligible nonresponder rates. These rates were higher than those of Visicol® Tablets (Arm A), although the differences were not statistically significant. Further, Arm E (INKP-102; 48 g split dose) demonstrated comparable or better colon-cleansing efficacy when compared with high-dose treatments (60 g dose; Arms A, B, and C). On the other hand, dosages given only on the evening prior to the patient's colonoscopy demonstrated poorer efficacy than those doses given as "split doses." The lower-dose (42 g) evening-only regimen of Arm F, only had a 72% responder rate, which was significantly lower than Arms B, C, and E (P<0.05; Fisher's Exact test).

Safety

The safety of the various dosing regimens was also evaluated by adverse event monitoring, changes in clinical laboratory evaluations, physical examination, and vital signs assessment (heart rate, blood pressure, respiratory rate, temperature, and testing for postural hypertension). No patients experienced a serious adverse event during the course of the study. Nearly all patients experienced mild to moderate adverse events related to the system organ class of gastrointestinal disorders, regardless of dosage or treatment. Such adverse events included abdominal distention, nausea, and abdominal pain. However, because the purpose of the treatment is to rapidly eliminate bowel contents, such events were to be expected.

Significant changes in clinical laboratory parameters from Visit 0 (screening) to Visit 1 (colonoscopy) were observed in all patient groups. Specifically, there was a significant increase (P<0.0001) in mean levels of inorganic phosphorus in all patient groups. There was a significant increase in mean levels of sodium in 6 of the 7 patient groups (P<0.02) and a significant decrease of BUN, potassium, calcium, magnesium, and bicarbonate from baseline in one or more patient groups (P<0.05). Mean levels of chloride and creatine in all patients, on the other hand, did not significantly change from baseline after treatment.

Of all the clinical parameters examined, only levels of inorganic phosphorus exhibited a significant, after-treatment difference between the INKP-102 and Visicol® treatment arms. Increases from baseline in inorganic phosphorus were anticipated and occurred with a mean increase of 88% over baseline levels in all patients, regardless of treatment arm. These increases in inorganic phosphorus levels were significantly higher among Arm A (Visicol® Tablets) than in patients in treatment arms D, E, F, and G (INKP-102; P<0.0170). The inorganic form of phosphate in the circulating plasma is excreted almost entirely by the kidneys and therefore some patients, such as those with renal disease, may have difficulty excreting a large phosphate load. Thus, use of INKP-102 beneficially reduces the burden on the kidneys during sodium phosphate treatment. This effect may be attributable to the reduced sodium phosphate doses in Arms D, E, F, and G. As described in several efficacy analyses above, however, INKP-102 more effectively cleanses the colon than a larger sodium phosphate dose of Visicol®, while at the same time reducing the increase in inorganic phosphorous normally observed with Visicol® administration.

All references cited herein are incorporated herein by reference in their entirety and for all purposes to the same extent as if each individual publication or patent or patent application was specifically and individually indicated to be incorporated by reference in its entirety for all purposes. To the extent publications and patents or patent applications incorporated by reference contradict the disclosure contained in the specification, the specification is intended to supercede and/or take precedence over any such contradictory material.

All numbers expressing quantities of ingredients, reaction conditions, and so forth used in the specification and claims are to be understood as being modified in all instances by the term "about." Accordingly, unless indicated to the contrary, the numerical parameters set forth in the specification and attached claims are approximations that may vary depending upon the desired properties sought to be obtained by the present invention. At the very least, and not as an attempt to limit the application of the doctrine of equivalents to the scope of the claims, each numerical parameter should be construed in light of the number of significant digits and ordinary rounding approaches.

Many modifications and variations of this invention can be made without departing from its spirit and scope, as will be apparent to those skilled in the art. The specific embodiments described herein are offered by way of example only and are not meant to be limiting in any way. It is intended that the specification and examples be considered as exemplary only, with a true scope and spirit of the invention being indicated by the following claims.

We claim:

1. A colonic purgative formulation in a solid dosage tablet form comprising:
   (a) sodium phosphate; and
   (b) between 7.5% and 15% of polyethylene glycol by weight, wherein the polyethylene glycol has an average molecular weight of 7,000 to 9,000 daltons and is uniformly distributed in the tablet so that the polyethylene glycol binds the sodium phosphate together to maintain the tablet form, and wherein a dosage of the formulation comprises 42-60 grams of sodium phosphate, and wherein the tablet form is for oral administration.

2. The formulation of claim 1, wherein the sodium phosphate comprises monobasic sodium phosphate, dibasic sodium phosphate, or a combination thereof.

3. The formulation of claim 1, wherein the tablet comprises a lubricant.

4. The formulation of claim 3, wherein the lubricant comprises magnesium stearate.

5. A colonic purgative formulation in tablet form comprising:
   (a) sodium phosphate monobasic from 45 to 75% by weight;
   (b) sodium phosphate dibasic from 15 to 30% by weight;
   (c) polyethylene glycol 8,000 from 5 to 20% by weight, wherein the polyethylene glycol provides a matrix upon which the sodium phosphate monobasic and sodium phosphate dibasic associate together to maintain the tablet form; and
   (d) magnesium stearate from 0.10 to 1.50% by weight, and wherein all of the weights are based on the total weight of the formulation.

6. A colonic purgative formulation in tablet form, comprising:
   (a) sodium phosphate from 15 to 90% by weight;
   (b) polyethylene glycol 8,000 from 5 to 20% by weight, wherein the polyethylene glycol provides a matrix upon which the sodium phosphate associates to maintain the tablet form; and
   (c) magnesium stearate from 0.10 to 1.50% by weight, and wherein all of the weights are based on the total weight of the formulation.

7. A kit comprising a colonic purgative formulation in tablet form for oral administration, wherein each tablet comprises:
   (a) at least one soluble binder comprising 5 to 20% polyethylene glycol, wherein the polyethylene glycol has an average molecular weight of 7,000 to 9,000 daltons; and
   (b) about 1.5 grams of sodium phosphate wherein the polyethylene glycol is distributed throughout the tablet so that the polyethylene glycol binds the sodium phosphate together to maintain the tablet form.

8. The formulation of claim 1, wherein the polyethylene glycol has an average molecular weight of 8,000.

9. The formulation of claim 1, wherein the polyethylene glycol comprises 10% by weight of the formulation.

10. The formulation of claim 1, wherein the tablet disintegrates within about 11 minutes.

11. The formulation of claim 1, wherein the formulation comprises 48 g of sodium phosphate divided between 32 tablets.

12. The formulation of claim 11, wherein the dosage comprises 20 tablets of the formulation being taken as 4 tablets at a time with 8 ounces of clear liquid every 15 minutes an evening before a colonoscopy.

13. The formulation of claim 11, wherein the dosage comprises 12 tablets of the formulation being taken as 4 tablets at a time with 8 ounces of clear liquid beginning 3 to 5 hours before a colonoscopy.

14. The formulation of claim 1, wherein mean increase from baseline of inorganic phosphorus levels occurs after administration of the formulation.

15. The formulation of claim 1, wherein the dosage produces mild catharsis.

16. A colonic purgative formulation in tablet form for oral administration wherein each tablet comprises 7.5% to 15% polyethylene glycol as a binder and about 1.5 grams of sodium phosphate, wherein the polyethylene glycol is admixed with the sodium phosphate in the tablet so that the polyethylene glycol binds the sodium phosphate together to maintain the tablet form and wherein the polyethylene glycol has an average molecular weight of 7,000 to 9,000 daltons.

17. The formulation of claim 16, wherein the tablet comprises about 1100 milligrams of sodium phosphate monobasic.

18. The formulation of claim 16, wherein the tablet comprises about 398 milligrams of sodium phosphate dibasic.

19. The formulation of claim 16, wherein the tablet comprises magnesium stearate.

20. The formulation of claim 16, wherein the tablet comprises about 8.4 milligrams of magnesium stearate.

21. The formulation of claim 16, wherein the tablet has a mass of about 1676 milligrams.

22. The formulation of claim 16, wherein the polyethylene glycol is polyethylene glycol 8000.

23. The formulation of claim 22, wherein the formulation comprises about 10% w/w of polyethylene glycol 8000.

24. A formulation in tablet form for oral administration, wherein each tablet comprises about 167 milligrams of polyethylene glycol having an average molecular weight between 7000 and 9000 daltons, about 1100 milligrams of sodium phosphate monobasic and about 398 milligrams of sodium phosphate dibasic.

25. The formulation of claim 24, wherein the polyethylene glycol is polyethylene glycol 8000.

26. The formulation of claim 24, further comprising magnesium stearate.

27. A purgative for cleansing a colon prior to a colonoscopy, the purgative comprising 48 grams of sodium phosphate in tablet form, wherein each tablet comprises about 1.5 grams of sodium phosphate and wherein the tablet also comprises 7.5% to 15% polyethylene glycol 8000, and wherein the polyethylene glycol is admixed with the sodium phosphate in the tablet so that the polyethylene glycol binds the sodium phosphate together to maintain the tablet form.

28. The purgative of claim 27, wherein each tablet comprises about 1102 milligrams of sodium phosphate monobasic and about 398 milligrams of sodium phosphate dibasic.

29. The purgative of claim 27, wherein each tablet comprises magnesium stearate.

30. The purgative of claim 27, wherein a dosage of the purgative comprises four tablets taken every 15 minutes.

31. A colonic purgative formulation in tablet form for oral administration, comprising sodium phosphate and polyethylene glycol, wherein the polyethylene glycol has an average molecular weight between 7000 and 9000 daltons and is distributed in the tablet so that the polyethylene glycol binds the sodium phosphate together to maintain the tablet form, the tablet made by a method comprising:
heating a mixture comprising the sodium phosphate and the polyethylene glycol to the melting point of the polyethylene glycol; and
compressing the formulation into a tablet.

32. The colonic purgative formulation of claim 31, wherein the polyethylene glycol is polyethylene glycol 8000.

33. The colonic purgative formulation of claim 31, wherein the mixture is allowed to cool down prior to compressing the formulation into a tablet.

34. The colonic purgative formulation of claim 33, wherein the mixture is allowed to cool down overnight prior to compressing the formulation into a tablet.

35. The formulation of claim 5, wherein the tablet disintegrates within about 11 minutes.

36. The formulation of claim 6, wherein the tablet disintegrates within about 11 minutes.

37. The formulation of claim 16, wherein the tablet disintegrates within about 11 minutes.

38. The formulation of claim 24, wherein the tablet disintegrates within about 11 minutes.

39. The formulation of claim 5, wherein the formulation comprises 32 tablets.

40. The formulation of claim 5, wherein the formulation comprises 40 tablets.

41. The formulation of claim 6, wherein the formulation comprises 32 tablets.

42. The formulation of claim 6, wherein the formulation comprises 40 tablets.

43. The formulation of claim 16, wherein the formulation comprises 32 tablets.

44. The formulation of claim 16, wherein the formulation comprises 40 tablets.

45. The purgative of claim 27, wherein the tablet comprises about 10% w/w of polyethylene glycol 8000.

46. The purgative of claim 27, wherein a dosage of the purgative comprises four tablets taken every 15 minutes for a total of 20 tablets the evening before a colonoscopy procedure.

47. The purgative of claim 27, wherein a dosage of the purgative comprises four tablets taken every 15 minutes for a total of 12 tablets the day of a colonoscopy procedure.

48. The formulation of claim 16 wherein the tablet binder consists essentially of polyethylene glycol.

\* \* \* \* \*